United States Patent
Inan et al.

(10) Patent No.: US 11,911,182 B2
(45) Date of Patent: *Feb. 27, 2024

(54) SYSTEMS AND METHODS OF IV INFILTRATION DETECTION

(71) Applicants: GEORGIA TECH RESEARCH CORPORATION, Atlanta, GA (US); CHILDREN'S HEALTHCARE OF ATLANTA, INC., Atlanta, GA (US); EMORY UNIVERSITY, Atlanta, GA (US)

(72) Inventors: Omer Inan, Atlanta, GA (US); Jambu Jambulingam, Atlanta, GA (US); Kevin Maher, Atlanta, GA (US); Russell Scott McCrory, Atlanta, GA (US); Leanne West, Atlanta, GA (US); Sinan Hersek, Atlanta, GA (US); Samer Mabrouk, Atlanta, GA (US)

(73) Assignees: Georgia Tech Research Corporation, Atlanta, GA (US); Children's Healthcare of Atlanta, Inc., Atlanta, GA (US); Emory University, Atlanta, GA (US)

( * ) Notice: Subject to any disclaimer, the term of this patent is extended or adjusted under 35 U.S.C. 154(b) by 183 days.

This patent is subject to a terminal disclaimer.

(21) Appl. No.: 17/505,848

(22) Filed: Oct. 20, 2021

(65) Prior Publication Data
US 2022/0039750 A1    Feb. 10, 2022

Related U.S. Application Data

(63) Continuation of application No. 16/311,459, filed as application No. PCT/US2017/039239 on Jun. 26, 2017, now Pat. No. 11,154,246.

(Continued)

(51) Int. Cl.
*A61B 5/00*    (2006.01)
*A61B 5/01*    (2006.01)
(Continued)

(52) U.S. Cl.
CPC .......... *A61B 5/6844* (2013.01); *A61B 5/0075* (2013.01); *A61B 5/01* (2013.01);
(Continued)

(58) Field of Classification Search
None
See application file for complete search history.

(56) References Cited

U.S. PATENT DOCUMENTS

| | | | |
|---|---|---|---|
| 4,898,576 A * | 2/1990 | Philip | A61M 5/16859 604/65 |
| 5,423,743 A | 6/1995 | Butterfield | |

(Continued)

FOREIGN PATENT DOCUMENTS

| | | |
|---|---|---|
| JP | 200007913 | 3/2000 |
| JP | 2000079103 A | 3/2000 |

(Continued)

OTHER PUBLICATIONS

Office Action received in Japanese Application No. 2019-519618 dated Mar. 29, 2022.

(Continued)

*Primary Examiner* — Carl H Layno
*Assistant Examiner* — Manolis Pahakis
(74) *Attorney, Agent, or Firm* — Meunier Carlin & Curfman LLC

(57) ABSTRACT

As an IV infiltration occurs and fluid leaks into surrounding tissues, several physiological changes are expected locally. The systems and methods described herein provide a scalable automated IV infiltration detection device to provide medical staff an early warning of a possible infiltration such (Continued)

that they can respond accordingly. The systems and methods capture the physiological state of the user at or around a peripheral catheter insertion site by incorporating one or more modalities of wearable sensing, processing the data collected from these wearable sensors, detecting the presence of extravascular fluid, and providing an indication to a medical professional.

21 Claims, 12 Drawing Sheets

Related U.S. Application Data

(60) Provisional application No. 62/354,357, filed on Jun. 24, 2016.

(51) Int. Cl.
  *A61B 5/0531* (2021.01)
  *A61B 5/11* (2006.01)

(52) U.S. Cl.
  CPC .......... *A61B 5/0531* (2013.01); *A61B 5/1114* (2013.01); *A61B 5/442* (2013.01); *A61B 5/7221* (2013.01); *A61B 5/746* (2013.01); *A61B 2560/0209* (2013.01); *A61B 2560/0223* (2013.01); *A61B 2562/0219* (2013.01); *A61B 2562/0261* (2013.01); *A61B 2562/0271* (2013.01)

(56) References Cited

U.S. PATENT DOCUMENTS

| | | | |
|---|---|---|---|
| 6,158,965 A | 12/2000 | Butterfield et al. | |
| 6,375,624 B1 | 4/2002 | Uber et al. | |
| 6,425,878 B1* | 7/2002 | Shekalim | A61M 5/16831 604/503 |
| 6,487,428 B1 | 11/2002 | Culver et al. | |
| 7,826,890 B1* | 11/2010 | Winchester, Jr. | A61B 5/0059 600/407 |
| 7,869,849 B2 | 1/2011 | Ollerdessen et al. | |
| 8,406,865 B2 | 3/2013 | McKenna et al. | |
| 8,515,515 B2 | 8/2013 | McKenna et al. | |
| 11,331,045 B1* | 5/2022 | Moschella | A61B 5/389 |
| 11,771,334 B1* | 10/2023 | Davis | A61B 5/02438 600/500 |
| 2002/0172323 A1 | 11/2002 | Karellas et al. | |
| 2003/0036674 A1* | 2/2003 | Bouton | H01Q 1/40 600/12 |
| 2003/0036713 A1 | 2/2003 | Bouton et al. | |
| 2003/0216663 A1* | 11/2003 | Jersey-Willuhn | A61B 5/412 977/932 |
| 2006/0135884 A1 | 6/2006 | Hack et al. | |
| 2007/0123770 A1 | 5/2007 | Bouton et al. | |
| 2007/0265521 A1 | 11/2007 | Redel et al. | |
| 2007/0276327 A1* | 11/2007 | Kalafut | A61M 5/16827 604/131 |
| 2008/0051648 A1 | 2/2008 | Suri et al. | |
| 2008/0224688 A1* | 9/2008 | Rubinsky | A61B 5/4244 324/76.77 |
| 2010/0305446 A1 | 12/2010 | Berard-Andersen et al. | |
| 2010/0331638 A1* | 12/2010 | Besko | A61B 5/7221 600/323 |
| 2011/0257522 A1 | 10/2011 | Berard-Andersen et al. | |
| 2013/0131506 A1 | 5/2013 | Pollack | |
| 2013/0237858 A1 | 9/2013 | Warren et al. | |
| 2013/0276785 A1* | 10/2013 | Melker | A61M 16/0677 128/204.23 |
| 2014/0343392 A1 | 11/2014 | Yang | |
| 2015/0073252 A1 | 3/2015 | Mazar | |
| 2015/0141774 A1 | 5/2015 | Ogawa et al. | |
| 2015/0335820 A1 | 11/2015 | De Armond et al. | |
| 2015/0351690 A1* | 12/2015 | Toth | A61B 5/291 600/391 |
| 2015/0366504 A1 | 12/2015 | Connor | |
| 2016/0080107 A1 | 3/2016 | Girouard | |
| 2016/0166207 A1 | 6/2016 | Falconer | |
| 2017/0340220 A1 | 11/2017 | Hsu et al. | |
| 2019/0298234 A1* | 10/2019 | Omenetto | G01N 27/028 |
| 2020/0202994 A1 | 6/2020 | Volkar et al. | |
| 2020/0230320 A1 | 7/2020 | Willybiro et al. | |
| 2022/0095940 A1* | 3/2022 | Banet | A61B 5/02141 |
| 2023/0157552 A1* | 5/2023 | Thuering | A61B 5/0205 600/301 |

FOREIGN PATENT DOCUMENTS

| | | |
|---|---|---|
| JP | 2005532841 | 8/2003 |
| JP | 2009508582 | 3/2007 |
| JP | 2009534122 | 11/2007 |
| JP | 2013017606 A | 1/2013 |
| JP | 2015504338 | 11/2014 |
| JP | 201442579 | 5/2015 |
| WO | 2003063680 | 8/2003 |
| WO | 2007035339 | 3/2007 |
| WO | 2007124298 | 11/2007 |
| WO | 2015034104 | 3/2015 |
| WO | 2016126856 | 8/2016 |

OTHER PUBLICATIONS

International Search Report and Written Opinion dated Sep. 15, 2017, from International Application No. PCT/US2017/039239, 9 pages.

International Preliminary Report on Patentability issued for International Application No. PCT/US2017/039239, dated Jan. 3, 2019, 7 pages.

Extended EP Search Report dated Jan. 30, 2020, issued in related EP application No. 17816367.1, 6 pages.

Office Action dated Jun. 1, 2021, issued in Japanese Application No. 2019-519618, 12 pages. English translation included.

V. Paquette, R. McGloin, T. Northway, P. DeZorzi, A. Singh, and R. Carr, "Describing intravenous extravasation in children (dive study)," pp. 340-345, 2011.

R. J. Kumar, S. P. Pegg, and R. M. Kimble, "Management of extravasation injuries," ANZ Journal of Surgery, vol. 71, pp. 285-289, 2001.

D. Camp-Sorell, "Developing extravasation protocols and monitoring outcomes," Journal of Infusion Nursing, vol. 21, pp. 232-239, 1998.

P. H. T. Cartlidge, P. E. Fox, and N. Rutler, "The scars of newborn intensive care," Early Human Development, vol. 21, pp. 1-10, 1990.

D. Doellman, L. Hadaway, L. A. Bowe-Geddes, M. Franklin, J. LeDonne, L. Papke-O'Donnell, J. Pettit, L. Schulmeister, and M. Stranz, "Infiltration and extravasation: update on prevention and management," Journal of Infusion Nursing, vol. 32, No. 4, pp. 203-211, 2009.

H. Amano, Y. Nagai, T. Kowase, and O. Ishikawa, "Cutaneous necrosis induced by extravasation of arginine monohydrochloride," Acta dermato-venereologica, vol. 88, No. 3, pp. 310-311, 2008.

Medical Emergencies and Complications: IV Complications, Columbia University Center for Teaching and Learning, 20 pages.

R. Gudivaka, D. Schoeller, and R. F. Kushner, "Effect of skin temperature on multifrequency bioelectrical impedance analysis," Journal of Applied Physiology, vol. 81, No. 2, pp. 838-845, 1996.

\* cited by examiner

SYSTEMS AND METHODS OF IV INFILTRATION DETECTION

CROSS REFERENCE TO RELATED APPLICATIONS

This application is a continuation of U.S. patent application Ser. No. 16/311,459, filed Dec. 19, 2018, issued as U.S. Pat. No. 11,154,246, which is a national stage application filed under 35 U.S.C. § 371 of PCT/US2017/039239 filed Jun. 26, 2017, which claims benefit to U.S. Provisional Patent Application Ser. No. 62/354,357, filed Jun. 24, 2016. Each of these applications is hereby incorporated by reference in their entireties for all purposes.

BACKGROUND

Embodiments of the present disclosure relate to a system and method for detecting infiltration of intravenous fluid into surrounding tissues.

Intravenous (IV) therapy is common among hospitalized patients, and allows rapid and effective delivery of drugs, volume expanders, blood-based products, and nutrition to the systemic circulation directly through the peripheral veins. IV infiltration (or extravasation), where fluid enters the surrounding tissue rather than the vein as intended, occurs in 0.1% to 6.5% of all hospital inpatients—though the actual incidence may be much higher due to inconsistent reporting/documentation—and in an even larger percentage of pediatric patients. Infiltration occurs as a result of a combination of issues, including solution osmolality, tissue toxicity, vasoconstrictor properties, infusion pressure, regional anatomical variability, and mechanically puncturing the lining of the vein. The effects can be devastating and include swelling, blistering, pain, and even tissue necrosis. Resulting injuries are considered to be medical emergencies and require immediate treatment. While there are treatments that can be administered to palliate these side effects, early detection remains the only effective method for preventing serious complications of IV infiltration.

Currently, IV infiltration is detected either by a nurse witnessing the signs first hand or by the patient alerting the medical staff of any symptoms. For example, adult patients will likely inform the nurse of any pain or swelling related to an infiltration and request repositioning or removal of the catheter.

However, when the nurse does not have a clear line of sight of the IV catheter site, or the patient is unable to communicate with medical staff, infiltrations can potentially be missed. This is often the case when the patient is under anesthesia, undergoing surgery and draped, or otherwise unable to communicate.

Children may not be able to communicate adequately, and thus infiltration may go unnoticed for prolong periods. This delay can result in major skin, muscle and tendon compromise locally that can cause debilitating short-term and long-term problems. Many such complications can be relatively straightforward to detect and rectify if the injection site is continuously observed and compared to the contralateral side.

Unfortunately, in many situations, including during a surgical procedure in the operating room, several factors greatly increase the risk of devastating IV infiltration. A child may be anaesthetized and unable to communicate, the IV site may be covered by drapes, and the surgical staff has little to no access to the site during the procedure. Small children often have IV sites heavily bandaged to maintain the IV and prevent it from being removed by the patient, such that the caregivers' ability to access infusion sites is compromised.

Detecting IV infiltration among infants is yet more challenging, since infants are not able to specifically communicate pain or discomfort to the nursing staff. Though infiltration can cause harm in adults, the effects of infiltration on children can be especially detrimental due to their smaller body size. The nurses in pediatric care are handling needs of many infants at any given time, and it becomes difficult for the nurse to identify an infiltration in a short time span. Continuously monitoring infants in the Neonatal Intensive Care Unit (NICU) is critical, and a complication like this can easily turn around the health of an otherwise healthy infant.

Prior technology for detecting IV infiltration exists, but often does not provide timely recognition of the infiltration and therefore does not prevent sequelae. The current technologies are also subject to a high occurrence of false positives and negatives. Some technologies for detecting IV infiltration utilize optical sensors. This principle of detection emits light from an emitter to the tissue to be monitored which is then reflected back by the tissue and detected using a detector. The reflected light signals are analyzed in order to detect infiltration. One problem with this technology is that optical signals are prone to motion artifacts. As a patient moves, the motion will alter the light reflected back by the tissue and deteriorate signal quality, making infiltration detection difficult. Another problem with this technology is potential difficulty in detecting fluids which might not alter the light reflected back by the tissue.

Prior technology that monitors skin temperature for infiltration detection exists (for example, see U.S. Pat. No. 6,375,624). These technologies use skin surface temperature sensors or microwave radiometry to monitor tissue temperature near the infiltration site. This principle of detection presents a difficulty as the injected fluid temperature and the surrounding tissue temperature are similar after thermal equilibrium in the monitored tissue is reached, whether infiltration occurs or not. The temperature signals can also be affected negatively by limb motion as the temperature sensor rubs the skin or intermittently loses contact during motion.

Methods of infiltration detection based on medical imaging also exist (for example, see U.S. Patent Application Publication No. 2002/0172323). Such systems use low dosage x-rays or ultrasound to detect infiltration. X-ray based detection involves radiation and ultrasound imaging cannot be used to monitor the tissue continuously. These methods also require a trained professional to operate the detection devices.

Accordingly, there is a need to improve timeliness of infiltration detection.

BRIEF SUMMARY OF THE INVENTION

Accordingly, the present invention is directed to systems and methods of IV infiltration detection that obviates one or more of the problems due to limitations and disadvantages of the related art.

In accordance with the purpose(s) of this invention, as embodied and broadly described herein, this invention, in one aspect, relates to systems and methods for capturing the physiological state of a user at or around a peripheral catheter insertion site. A system for performing these methods can include multiple modalities of wearable sensors, a processor in electrical communication with the multiple modalities of wearable sensors, and an indicator configured to provide an indication of the presence of extravascular fluid. The processor is configured to run an algorithm to process sensor data collected from the multiple modalities of wearable sensors and to detect the presence of extravascular fluid.

Additional advantages of the invention will be set forth in part in the description which follows, and in part will be obvious from the description, or may be learned by practice of the invention. The advantages of the invention will be realized and attained by means of the elements and combinations particularly pointed out in the appended claims.

Further embodiments, features, and advantages of the systems and methods for detecting IV infiltration, as well as the structure and operation of the various embodiments of the systems and methods for detecting IV infiltration, are described in detail below with reference to the accompanying drawings.

It is to be understood that both the foregoing general description and the following detailed description are exemplary and explanatory only, and are not restrictive of the invention as claimed.

DETAILED DESCRIPTION OF THE INVENTION

Figure 1:
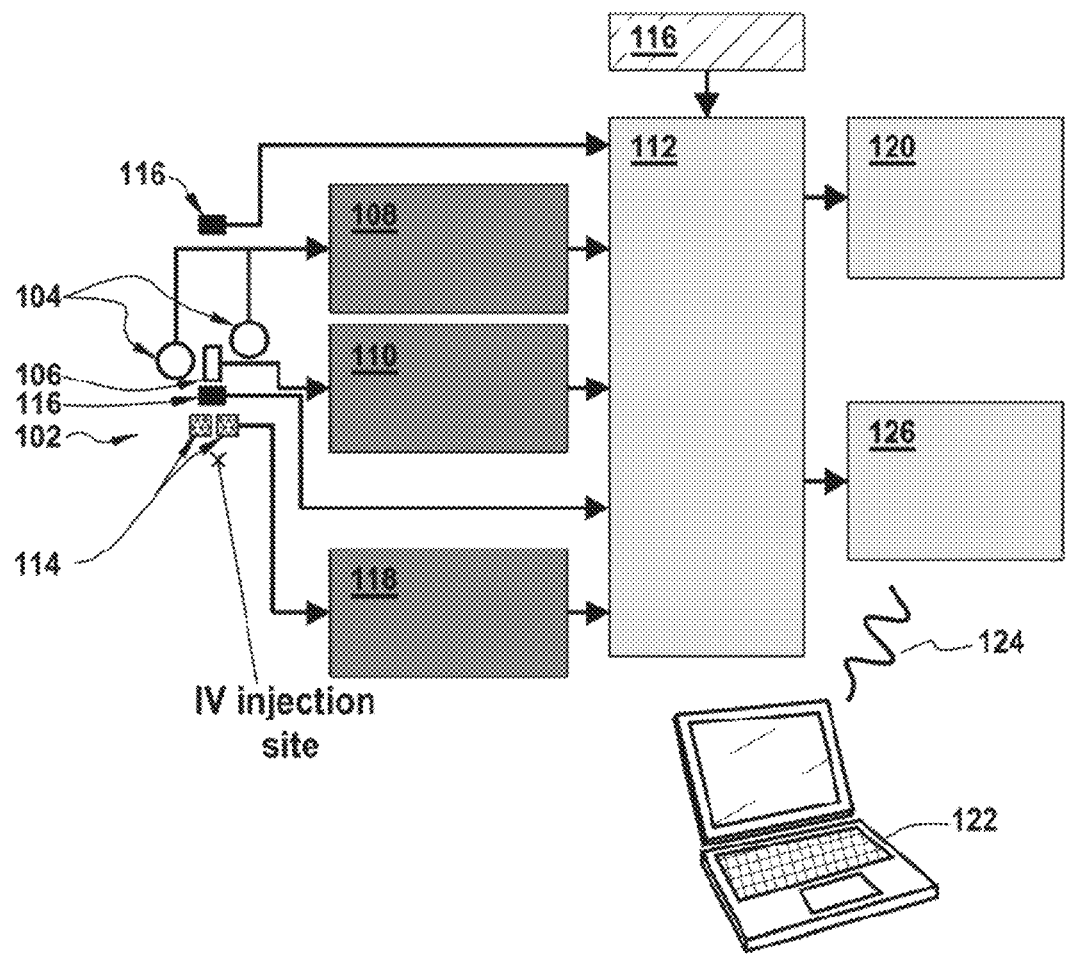
FIG. 1 is a block diagram of an exemplary hardware architecture of a system according to principles of the present disclosure.

Reference will now be made in detail to embodiments of the systems and methods of IV infiltration detection with reference to the accompanying figures.

The system design described herein provides a scalable automated IV infiltration detection device to provide medical staff an early warning of a possible infiltration such that they can respond accordingly. As an infiltration occurs and fluid leaks into surrounding tissues, several physiological changes are expected locally. In a manner of tens of minutes, the overall shape and composition of the IV site (hand, foot, arm, etc.) can change dramatically following an infiltration, as the interstitial space is filled with fluid from the IV. Additionally, since the temperature of the IV fluid is typically lower than skin temperature for a patient in a hospital room, the local skin temperature will decrease. Accordingly, caregivers are trained to "look, feel and compare (to the contralateral side)" to detect, as early as possible, an infiltration. These changes that are readily perceptible to the caregivers are a result of swelling, cooling, and discoloration (due to cutaneous vasoconstriction associated with the swelling and cooling, being more prominent with vasoactive agents).

A sensing scheme as described herein aims to continuously examine the local physiological symptoms of infiltration: sensing physiology rather than attempting to place sensors on the IV needle itself, which can allow the technology to be rapidly translated into clinical settings upon successful demonstration and provide better sensitivity as the flow rate from the IV is slow, and the pressures/flows may not change significantly with an infiltration; using multi-modal non-invasive sensing to maximize sensitivity and specificity; leveraging knowledge of peripheral vascular physiology to create solutions that would be less obtrusive and more rapidly translated to clinical use than any other competing technology; and differentially analyzing both sides of the body simultaneously to differentiate between systemic versus local physiological variations. The non-invasive signs of IV infiltration that can potentially be measured include the swelling of soft tissue and increased skin firmness, and other modalities indicative of IV infiltration, such as electrical bioimpedance (EBI), skin temperature, strain, motion, position, and reflectance. By using low power sensors and embedded processing, the sensing device could remain attached to the body and use wireless communication with the medical staff's host devices.

An automated detection system using non-invasive sensing of bioimpedance and strain around the catheter site may include high-resolution, wireless sensors. Local skin temperature may also be measured as an indication of IV infiltration, depending on the temperature of the fluid being infused into the patient by the IV. Optical sensors can help by providing near infrared and reflectance photoplethysmogram measurements. Motion or inertial sensors, such as accelerometers, gyroscopes, and/or magnetometers can be included to detect motion artifacts in other sensing modalities. While one sensor may be used alone, multiple sensing modalities can provide a synergistic effect by offering additional insight into a questionable or alarming sensor reading. As one example of this synergistic effect, a bioimpedance measurement may change if a patient flips their wrist over. A motion or inertial sensor can be used to indicate to the caregiver that the questionable sensor reading coincided with a movement from the patient, and may not actually indicate infiltration. By combining non-invasive sensing with a low power embedded processing system, this device could be mechanically designed to sit around the catheter site for long periods of time without impeding the patient's mobility. The availability of low-cost sensors and microprocessors allow for an economically feasible solution for all types of medical care.

FIG. 1 is a block diagram of an exemplary hardware architecture of a system according to principles of the present disclosure. In this exemplary architecture, information/data collected from a patient's body part, e.g., a wrist or hand 102, is collected, for example, via a bioimpedance sensor 104 and a strain gauge 106. Collected data from the bioimpedance sensor 104 and strain gauge 106, provided through analog "front-end" interfaces 108, 110, are input to a processor, such as a microcontroller 112. Other information may be collected and provided to the microcontroller, such as reflectance 114 and additional temperature information 116, through appropriate "front end" interfaces 118. The microcontroller 112 may have a battery backup 116, as well as connection to A/C power (not shown). The microcontroller 112 may output data to a storage device 120, such as an SD card or to an external computer, laptop, or tablet 122 via a wired or wireless connection 124, such as a Bluetooth low energy transmission 126 or other wireless communication interface.

Figure 2A:
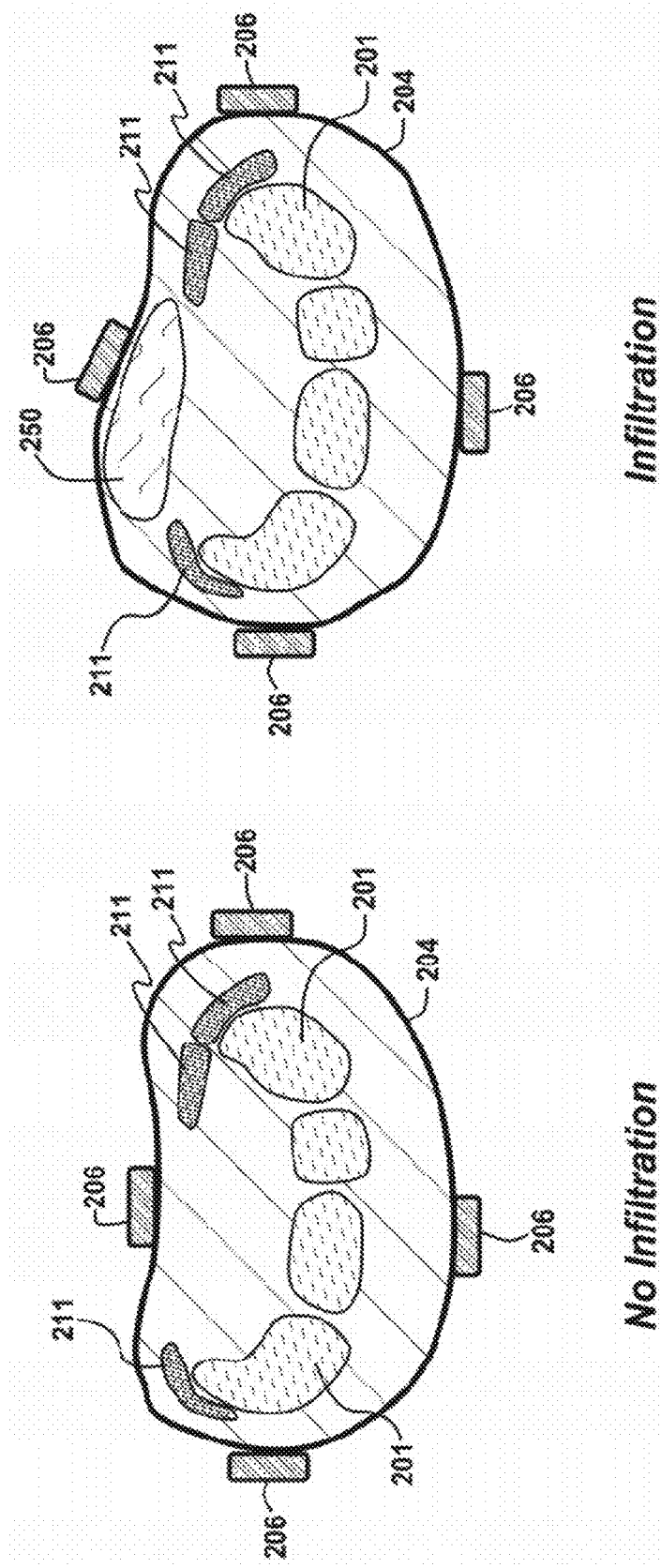
FIG. 2A illustrates a cross section of the arm near the wrist, with (right side) and without (left side) infiltration.
Figure 2B:
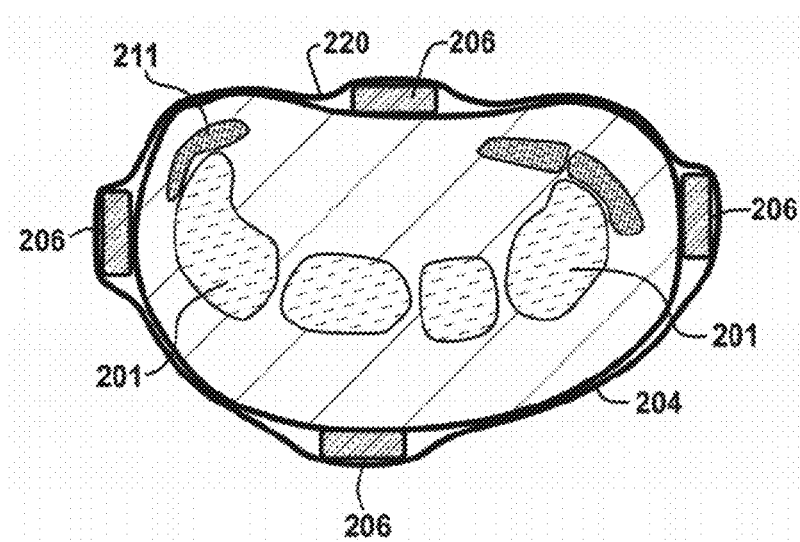
FIG. 2B illustrate the placement of strain gauges when using a fitted sleeve.

In one modality, the swelling of soft tissue can be modeled as stretching of the skin surrounding the IV catheter. The fluid leaking into the soft tissue causes the skin to expand radially. FIG. 2A illustrates a cross section of the arm near the wrist 204 and for purposes of example includes representations of the bones 201 and muscle 211 of the wrist 204. To sense this swelling, a network of strain gauges 206 may be placed around the IV catheter site, as illustrated in FIG. 2A. A full-bridge topology may be used in this application for its temperature compensation effect. This topology may use four strain gauges 206 that can all be actively sensed, which allows the system to use a single full bridge input to capture strain measurements radially at the IV catheter site. As illustrated in FIG. 2A, infiltrated fluid 250 under the skin displaces the strain gauge 206. The strain gauges can be placed equidistant from one another and orthogonal to the length of the arm, to measure skin stretching anywhere around the site. The strain gauges may be placed with same Z-axis orientation, such that the pattern is facing outwards and the backing material is in contact with the skin. Such configuration allows changes in strain to be calculated for with the correct sign convention. The gauges may be mounted on a neoprene compression sleeve around the catheter site, with enough compression to make the gauges abut the skin, and may be "skin-tight." FIG. 2B illustrates the placement of strain gauges 206 when using a neoprene sleeve 220 for placement of the sensor suite, including the strain gauges 206. The sensors described herein can be placed into contact with the patient via a sleeve formed of neoprene or any other material. A sleeve or wrap can, in some embodiments can be closed using hook and loop fasteners (such as Velcro®), hook and eye fasteners, zippers, or any other closure mechanisms that can be used in the medical setting. In some embodiments, the sensors can be applied to the patient using adhesive patches or bandages.

Increased skin firmness content due to fluid leakage can be captured by measuring the change in bioelectrical impedance around the IV catheter site. A localized increase in conductive IV fluids can reduce the measured impedance. Known as bioimpedance analysis, this technique uses a small, safe alternating electrical current to measure a potential difference between electrodes placed on the body to determine body composition in a target area. The measured impedance can be modeled by a network of resistors and capacitors. EBI spectroscopy can also be utilized, which measures impedance at different frequencies to enhance EBI analysis. To further enhance detection, the EBI measured at the catheter insertion site can be compared to the EBI measured at another "control" site, such as the limb without the catheter or another site on the same limb. Detection can also be enhanced by taking EBI measurements from multiple areas around the catheter insertion site.

Figure 3:
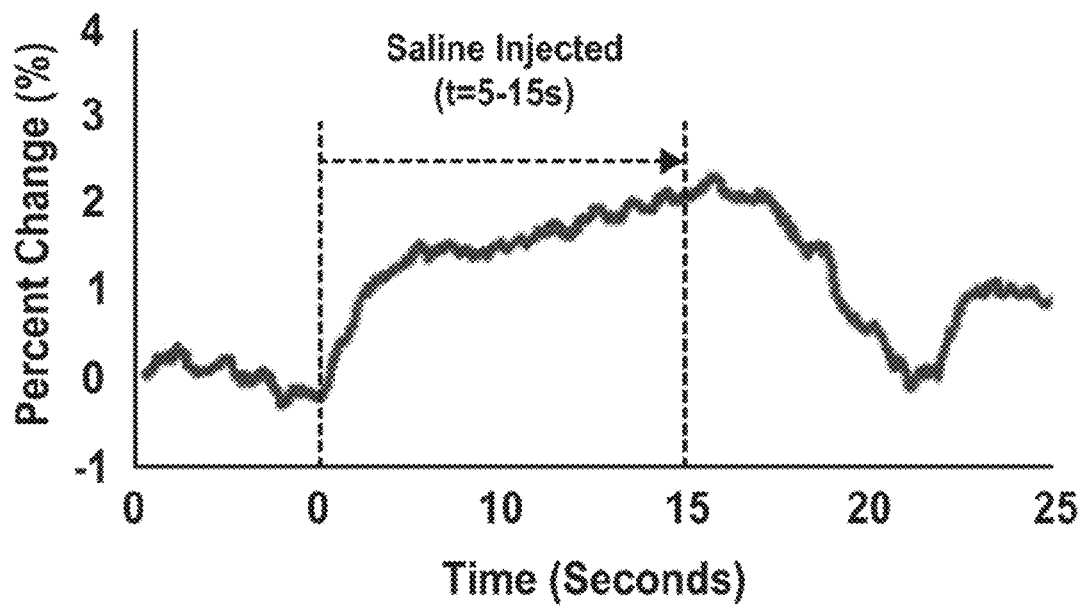
FIG. 3 is a graph showing measured percent change in radial strain after infusion of saline into soft tissue in an experimental study.

A graph showing measured percent change in radial strain after infusion of saline into soft tissue in an experimental study is provided at FIG. 3. In the experimental study illustrated, the infusion of saline solution began at t=5 s and ended at t=15 s. The maximum change is seen at the end of the infusion, measuring about 2.25% expansion of the strain gauge bridge.

The mechanical placement of the electrodes may be chosen, taking into consideration the IV catheter site and measurement technique. For example, a local bioimpedance sensor may be placed at the wrist at the distal radio-ulnar joint if the superficial dorsal vein is the venipuncture site, which is often used with infants. Tetrapolar measurements may be used for measuring impedance. Such tetrapolar measurements may be achieved using four separate electrodes, e.g., a pair for current excitation and one for voltage sensing. The electrodes may be placed symmetrically around the IV site.

Figure 4:
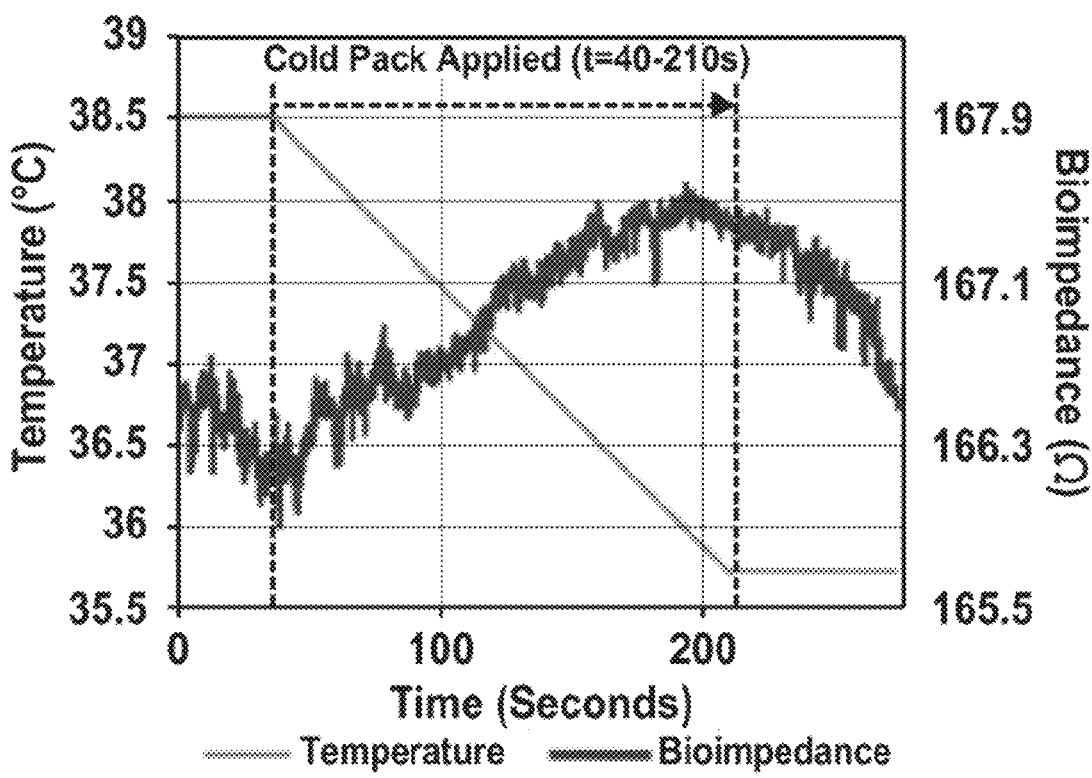
FIG. 4 is a graph showing measured percent change in radial strain after infusion of saline into soft tissue in an experimental study.

The relationship between bioimpedance and temperature has been tested by rapidly cooling a section of skin and measuring its real impedance. FIG. 4 is a graph showing change in bioimpedance at a site in-between electrode cuffs based on the rapid change in skin temperature plotted against a linear extrapolation of skin temperature based on recordings from the beginning and the end of an experiment. An ice pack was place on the skin at t=40 s and removed at t=210 s. The negative correlation between skin temperature and bioimpedance is seen within this timeframe. The test set-up used a frozen ice-pack and electrode cuffs constructed for the patient's arm radium. The contact between the dry copper electrodes and skin had to be tight to reduce the resistivity associated with the electrode interface. Hence, a large strip of copper tape was wrapped around the arm and secured using Velcro straps. The impedance change resulting from a sharp decrease in temperature may be only about ±1Ω from the resting impedance of the skin section, but it can be well within the range of interest when an infusion of liquid results in a change with the same order of magnitude.

Detecting IV infiltration may be performed by monitoring stretching of the skin proximal to the infiltration site and the reduction in bioimpedance. Monitoring of both of these effects can be performed non-invasively. The detection speed of the system allows for a device that can help alert a nurse of an infiltration before the solution has leaked into the nearby tissue. The redundancy of monitoring both the skin stretching and the reduction in bioimpedance may reduce false positives and/or may help maintain a fast response time. Good detection speed can help alert medical staff of an infiltration early, for example, before significant leakage into nearby tissue.

Electrical bioimpedance (EBI) measurement as a predictor of IV infiltration correlates with vasoconstriction. For example, EBI measurements have been shown recently to be indicative of minor local edema from musculoskeletal injury, and thus should be sufficiently sensitive to detect changes in tissue impedance related to fluid accumulation from an IV infiltration. The location of EBI electrodes for detecting IV infiltration may include one of each an excitation current electrode and a voltage sensing electrode on the wrist by the radial artery. Two additional electrodes may be placed on the opposite side of the wrist to provide measurement of the EBI across the wrist, which would be reduced by the increased presence of fluid resulting from infiltration. Other differential components comparing one side of the body to another may be used.

Figure 5A:
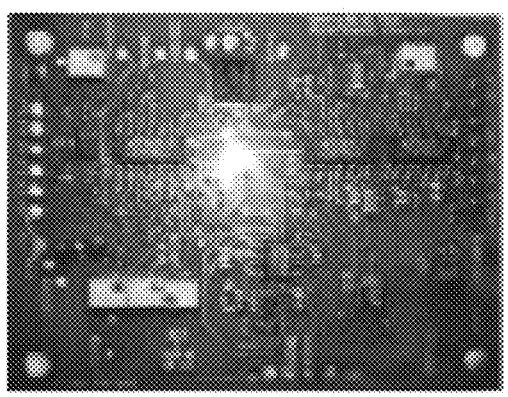
FIG. 5A illustrates an exemplary EBI measurement circuit.
Figure 5B:
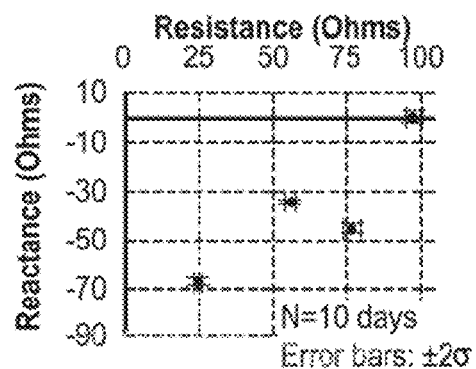
FIG. 5B is a graph showing data points measured using the exemplary EBI measurement circuit of FIG. 5A.
Figure 5C:
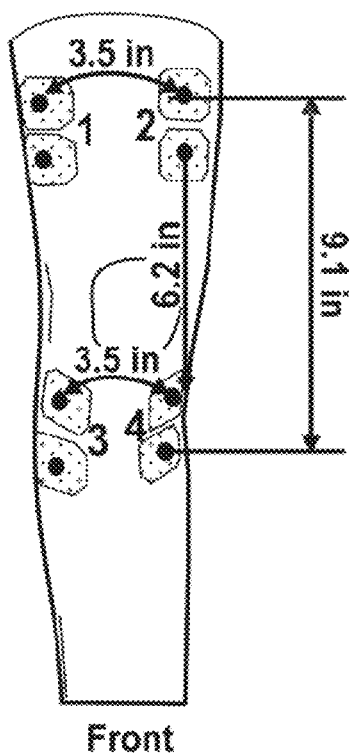
FIG. 5C shows example electrode positions for the knee-based bioimpedance measurements.

FIGS. 5(a)-(g) show contemporary EBI hardware developed for assessing local physiology at the knee. The location of four EBI electrodes for detecting IV infiltration have been determined through experimentation. The location provides good positioning both in terms of comfort for the patient and in properly detecting the infiltration. Similar techniques have been used by the inventors for experimentally determining optimal electrode positioning for the knee, as shown in FIG. 5(c). E.g., a four electrode Kelvin sensing scheme may be used with a small, safe, AC current excitation to two electrodes (I=1 $mA_{pp}$, $f_c$=50 kHz); and the resultant AC differential voltage measured across the other two electrodes. The distances between electrodes shown in FIG. 5(c) are one exemplary embodiment, but other distances between electrodes may be utilized in other embodiments. The ratio of the measured voltage to the injection current will provide the impedance soft the tissue, with the skin-electrode impedance being removed. These techniques have been shown to provide substantially accurate, substantially linear and substantially consistent measurements of EBI, as illustrated in FIGS. 5(b) and (e). Placing one each of the excitation current and voltage sense electrodes on the wrist by the radial artery and the other two on the opposite side provides a relevant signal: a measurement of EBI across the wrist, which would be reduced by the increased presence of fluid (a highly conductive medium) due to infiltration.

Figure 5D:
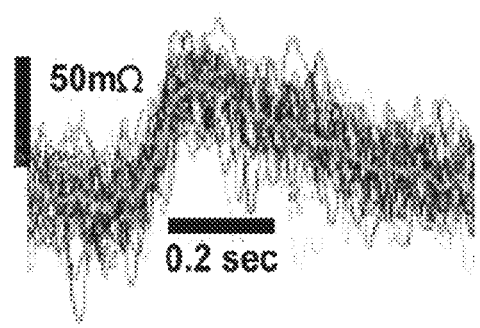
FIG. 5D is a graph showing the sensitivity of the exemplary EBI measurement circuit of FIG. 5A. Several plethysmography (IPG) heartbeats are shown.
Figure 5E:
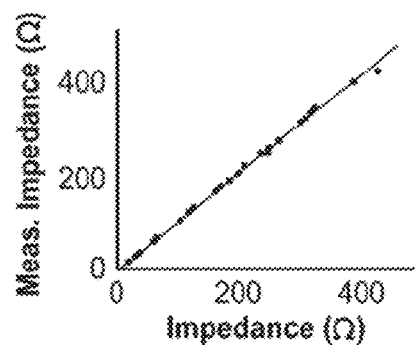
FIG. 5E is a plot of measured versus actual impedance values to demonstrate the linearity of the circuit of FIG. 5A.
Figure 5F:
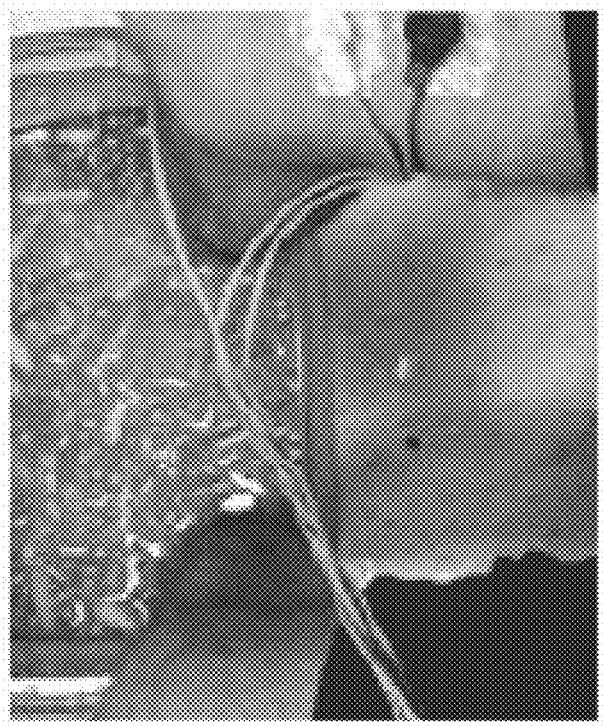
FIG. 5F shows a test setup for assessing downstream vasoconstriction using the exemplary EBI electrodes. A subject is placing his feet into ice water to model the vasoconstriction that occurs during infiltration.
Figure 5G:
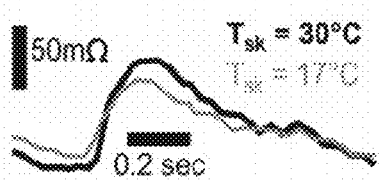
FIG. 5G is a graph showing that IPG heartbeat amplitudes decrease during the exposure to ice water shown in the test setup of FIG. 5F.
Figure 5H:
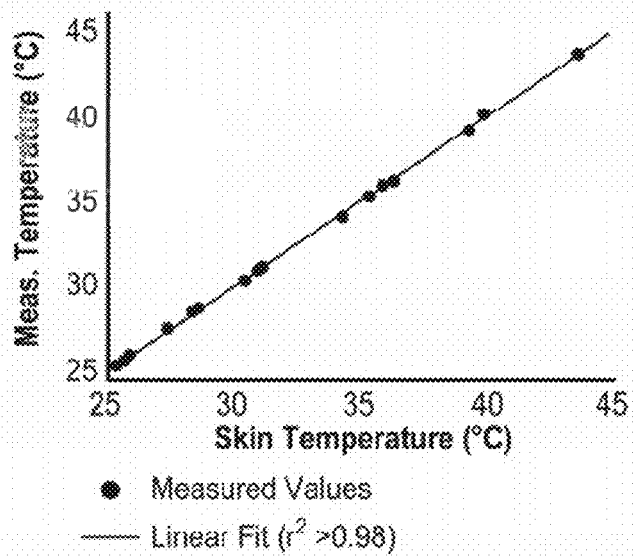
FIG. 5H is a graph showing the performance of resistance temperature (RTD) sensors with custom electronics.

FIG. 5(a) illustrates an exemplary EBI measurement circuit using commercial components and a novel high performance analog circuit design. FIG. 5(b) shows data point measured using the exemplary EBI measurement circuit of FIG. 5(a) in 10 separate measurement days to demonstrate consistency. Error bars show the 95% confidence interval of the impedance measurements both in resistive and reactive components. FIG. 5(c) shows example electrode positions for the knee-based bioimpedance measurements taken with the exemplary EBI measurement circuit of FIG. 5(a). FIG. 5(d) illustrates sensitivity of the exemplary EBI measurement circuit to detect very small (<100 mΩ) changes in bioimpedance that occur locally associated with the blood volume pulse (i.e., plethysmography, IPG). Several IPG heartbeats are shown. FIG. 5(e) is a plot of measured versus actual impedance values to demonstrate the linearity of the circuit for a wide range of impedance values. FIG. 5(f) shows a subject placing his feet into ice water while wearing the exemplary EBI electrodes at the knee to assess the effects of downstream vasoconstriction on the IPG heartbeat amplitudes. (The same type of downstream changes in peripheral vascular resistance are expected for IV infiltration). As illustrated in FIG. 5(g), the IPG heartbeat amplitudes decreased substantially while the subject's feet were immersed in the ice water as compared to taken out of the water. The corresponding skin temperature at the foot is shown for both cases. FIG. 5(h) shows performance of RTD-based temperature sensors with custom electronics previously designed for skin temperature measurements (0.1° C. resolution, 25-45° C. range).

Figure 6:
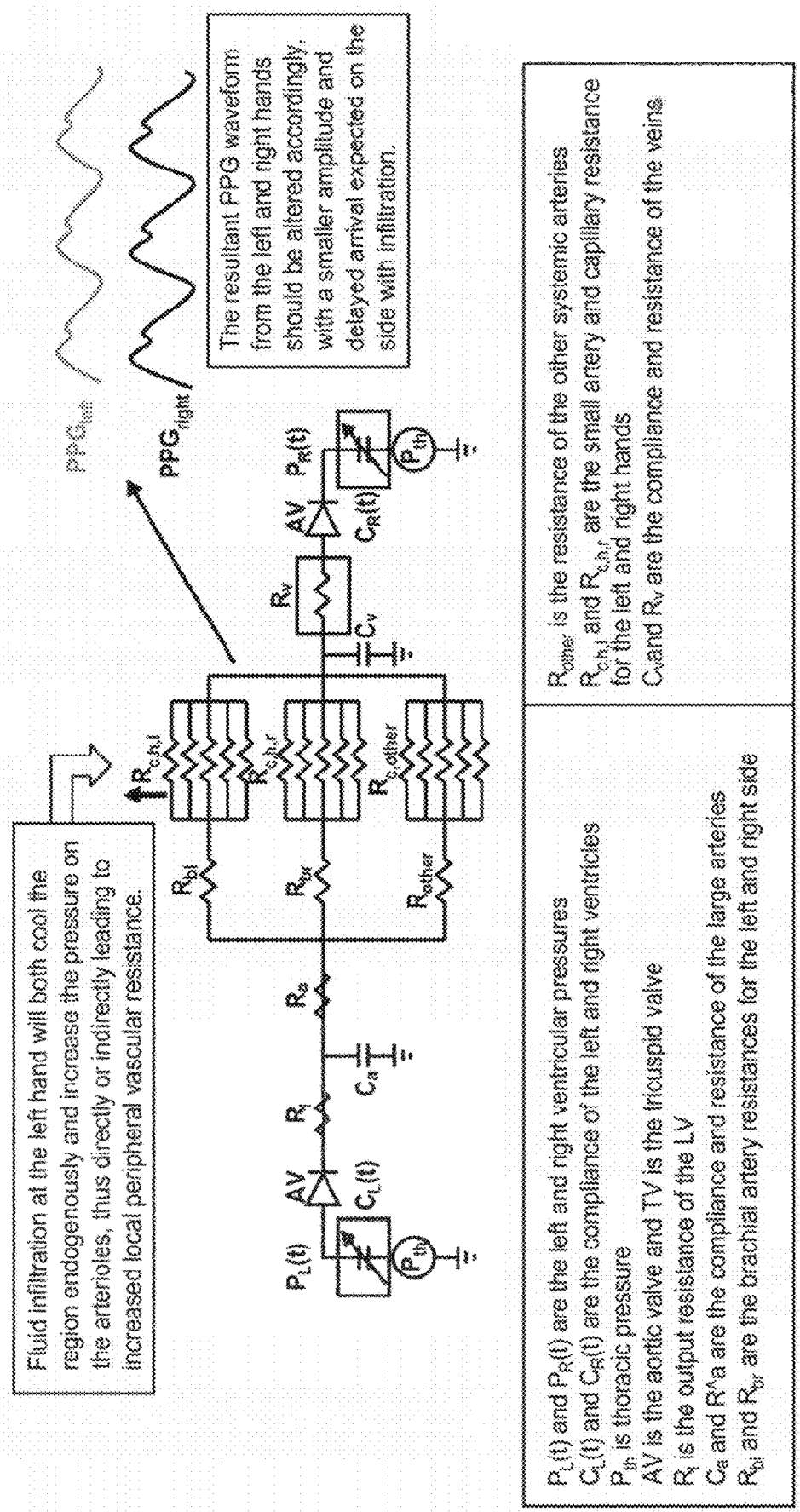
FIG. 6 shows a simplified lumped parameter model which provides physiological rationale for expecting changes in the photoplethysmogram (PPG) waveform on the side with IV infiltration compared to the contralateral side.

In addition to changes in EBI, the blood volume pulse components may decrease due to increased downstream peripheral vascular resistance (PVR) at the hand. This is based on models of the cardiovascular systems, such as the simplified lumped parameter model shown in FIG. 6, which provides physiological rationale for expecting changes in the photoplethysmogram (PPG) waveform on the side with IV infiltration compared to the contralateral side, as well as known local EBI measurements at the knee, e.g., resultant changes in EBI blood volume pulse component when a subject places his feet in a bucket of water to simulate such increased downstream PVR: the pulsatile component decreases in amplitude due to vasoconstriction. Hardware may be used to detect either or both in-phase and quadrature demodulation schemes to capture both the real and reactive part of the impedance changes. In FIG. 6, $P_L(t)$ and $P_R(t)$ represent left and right ventricular pressures. $C_L(t)$ and $C_R(t)$ represent the compliance of the left and right ventricles. $P_{th}$ represents thoracic pressure. AV represents the aortic valve. TV represents the tricuspid valve. $R_l$ represents the output resistance of the left ventricle. $C_a$ and $R_a$ represent the compliance and resistance of the large arteries. $R_{bl}$ and $R_{br}$ represent the brachial artery resistances for the left and right side. $R_{other}$ represents the resistance of the other systemic arteries. $R_{c,h,l}$ and $R_{c,h,r}$ represent the small artery and capillary resistance for the left and right hands. $C_v$ and $R_v$ represent the compliance and resistance of the veins. Fluid infiltration at the left hand will both cool the region endogenously and increase the pressure on the arterioles, thus directly or indirectly leading to increased local peripheral vascular resistance. The resultant PPG waveform from the left and right hands should be altered accordingly, with a smaller amplitude and delayed arrival expected on the side with infiltration.

In addition to blood volume pulse changes manifested in the EBI signal, an optical measurement (photoplethysmogram) (PPG waveform) of the blood volume changes in the microvascular tissue bed can be taken on both hands. A difference in the PPG waveform features on one hand compared to the other may indicate an IV infiltration. PPG waveforms are measured regularly in clinical practice for hospitalized patients, with systems better known as pulse oximeters. The PPG waveform is often measured at red and infrared wavelengths to calculate SpO2 and is continuously measured for most pediatric patients in the hospital. While the pulsatile component of the EBI signal corresponds to the blood volume pulse in the deeper arteries (e.g., radial artery), the reflectance PPG measures the corresponding blood volume pulse in the superficial cutaneous microcirculation. The combination of both provides the capability to differentiate between changes in local blood flow due to ambient temperature changes, which will affect the PPG more than the EBI signal, from those associated with edema and internal cooling from infiltration.

The PPG waveform may be processed to reduce baseline wander and high frequency noise using linear filtering and wavelet denoising techniques. As the PPG represents the blood volume pulse waveform, the cooling of the tissue and increased external pressure on the arterial wall for the arterioles should lead to a decrease in peak-to-peak amplitude. Heartbeat detection and ensemble averaging approaches to further reduce noise and motion artifacts may also be employed.

Optical measurements may also be used to detect infiltration. The leakage of fluid into the tissue may change the optical reflectance properties of the tissue itself, and may reduce the oxygenation locally (due to the edema restricting perfusion). Near infrared spectroscopy (NIRS), or the like, can measure a tissue oxygenation index, which is the ratio of oxygenated to total hemoglobin in the tissue. NIRS systems as well as time resolved spectroscopy (TRS) systems have been shown to accurately track changes in tissue oxygenation and may be used in the present system to detect and compare changes in tissue oxygenation in a body part with an IV catheter inserted therein and one without.

For PPG measurement, a reflectance mode can include a photodiode and LED positioned both on the same surface of the skin. This approach may reduce the overall footprint of the system by reducing the requirement for a PPG sensor on the finger of the patient. The photodiode and LED may interface with an analog front-end such as an AFE4400 (Texas Instruments, Dallas, Texas). The front-end may be connected to a microcontroller, for example, through serial communication (SPI).

Sensor measurements can be affected by motion and posture of the site that is measured. As an example, EBI of the wrist measured between two points can be different when the subject's palm faces up or down relative to their body. The impedance of the wrist can also change when the subject makes a fist versus when they relax their hands. The impedance signal starts varying as a subject moves the limb being measured, due to local impedance changes caused by limb motion. Therefore, it is useful to include sensors that measure limb motion, position, and inertia along with EBI signals. Accelerometers, gyroscopes, and magnetometers are a few exemplary sensors that can be used for position and motion tracking. These or other types of position or motion sensors can be used alone, or in combination with each other.

Sensing modalities other than EBI, such as strain sensors, optical sensing, and temperature sensing, are also prone to changes due to limb position and motion. Therefore, these sensing modalities can also benefit from use in combination with one or more motion, position, or inertial sensors, such as accelerometers, gyroscopes, and/or magnetometers, to indicate that a questionable reading may be a result of or influenced by movement. Information indicating limb movement may be used to adjust other measurements that might be influenced by movement, and thus reduce falsely positive indications of IV infiltration. One exemplary way of using the information from motion, position, or inertial sensors is to design a method of detecting when the measured limb is in motion and exclude those time instances from the analysis. The position of the limb devised using the information from motion, position, or inertial sensors can also be combined with other types of measurements to compensate for changes due to limb position. An exemplary way of doing this would be to detect when the subject's limb is in a certain position via a position sensor, and monitor the other sensor measurements taken in those time instances for detection. The position information may help the user understand otherwise questionable readings from the other sensors. The usage of motion, position, and inertial sensors is not limited to these examples provided.

Experimental Results and Exemplary Embodiment

In an exemplary system according to principles described herein, a sensing element may be designed to record up to 64 samples per second, such that time averaging methods can be used to increase detection specificity and sensitivity, while still enabling rapid response. The number of samples per second may range from 5 samples per second to well above 64 samples per second, depending on the capability of the circuit for fast sensing and computation. Averaging of the samples results may improve the quality of the results, particularly at lower sample rates.

Figure 7:
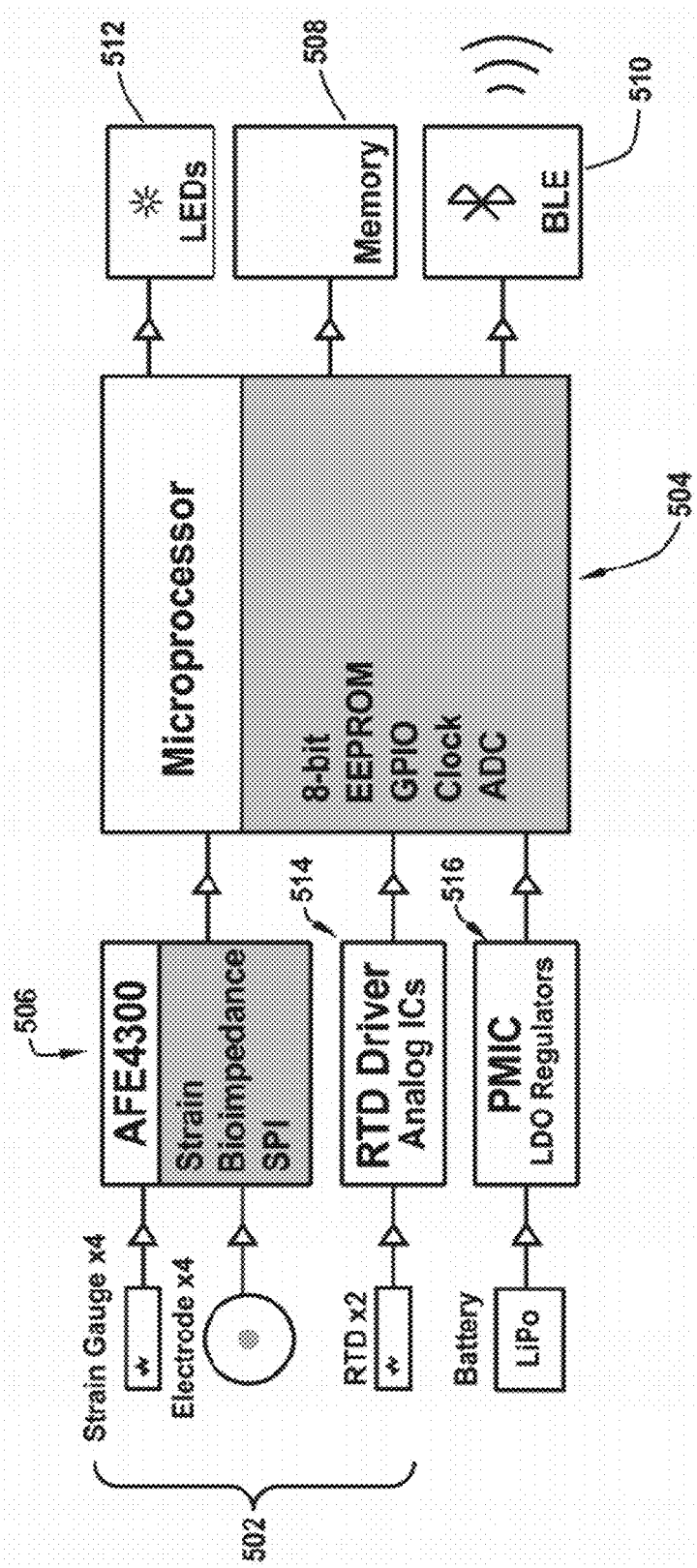
FIG. 7 shows a block diagram of an exemplary system.

An exemplary system is illustrated in block diagram in FIG. 7. In the exemplary architecture, peripheral sensors 502 are placed on the body with a microprocessor 504 and communications systems off the body. In other embodiments, the communications systems could also be positioned on the body. Commercially available electronic parts, such as a microprocessor 404 and an integrated analog front-end 506, may be used. For example, an exemplary microprocessor 504 may be an 8-bit AT mega 1284P (Atmel, San Jose, California). This exemplary microprocessor 504 may be 8 bit and include electrically erasable programmable read-only memory (EEPROM), general-purpose input/output (GPIO), a clock and an analog-to-digital converter (ADC) as appropriate. The exemplary microprocessor 504 includes minimal non-volatile memory on the microprocessor 504. An additional memory storage device 508 may be used without being powered. A secure digital (SD) card 508 may be used for data storage. A Bluetooth or other wireless transmission device 510 onboard may be used to allow communication between the device and a host computer for data processing. An indicator, such as an LED 512 or other device to alert medical staff, such as audible alarm, may be included in the device for alerting medical staff that the system has detected an IV infiltration.

An application specific integrated circuit, such as AFE4300 may be used as the analog front-end 506 for measuring bioimpedance and/or strain. The AFE4300 has low-power requirements. The AFE4300 also includes a Wheatstone bridge input with amplification circuitry and computes bioimpedance using a tetrapolar model of measuring voltage on a separate pair of electrodes near the electrodes used for current excitation. The gained output measurements are converted using an analog-to-digital converter, and the output is connected to the microcontroller using a serial-peripheral interface (SPI).

Figure 8:
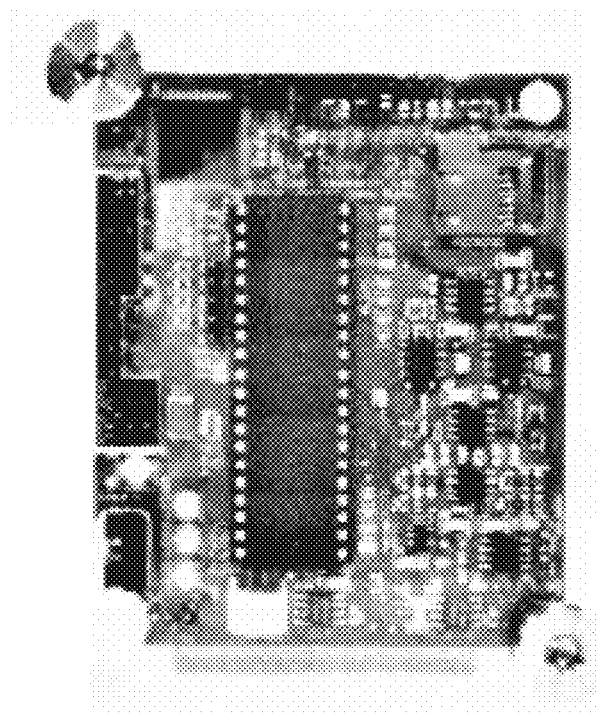
FIG. 8 illustrates an exemplary printed circuit board (PCB) with mechanical form factor for off-body use.

Since bioimpedance measurements can potentially be influenced by skin temperature, a skin temperature sensor can provide skin temperature measurements for the bioimpedance sensors. For example, as illustrated in FIG. 7, at least one resistance temperature sensor (RTD) 502 may be placed on the patient's skin. In an exemplary embodiment, two skin temperature sensors, e.g., RTDs, may be used—one in close proximity to the catheter site and one away from the catheter site as a control. The exemplary temperature sensor, RTD, includes circuitry designed to use a full range of ADC to measure temperatures between 0° C. and 50° C., where skin temperature generally rests around 37° C. The circuit may also include an RTD driver circuit 514 that conditions the signals from the RTD sensor (filtering, removing DC bias etc.) which is then to be recorded digitally and power management integrated circuits (PMICs) 516 for regulating the voltage from the battery as well as battery charging (for example with a USB charging cable) and shutting down the circuit if too much current is being consumed FIG. 8 illustrates an exemplary printed circuit board (PCB) with mechanical form factor for off-body use. This total current consumption, which represents always on, worst case current requirements, with continuous storage to the SD card and transmission of data via Bluetooth, if provided by 1000 mAh Lithium Polymer based battery, gives the device approximately 7 hours of use per charge, not including the use of sleep mode, which can readily be implemented in firmware. Table I contains the cumulative measure electrical specifications from the exemplary PCB.

TABLE 1

| Parameter | Typical | Unit |
| --- | --- | --- |
| System Voltage | 3.7 | V |
| System Supply Current | 130 | mA |
| Bioimpedance Operation | | |
| Noise | ±0.5 | Ω |
| Resolution | 3 | Ω |
| Dynamic Range | 0-2.8 | kΩ |
| Supply Current | 1 | mA |
| Strain Operation | | |
| Noise | ±1.22 | ° |
| Resolution | 5 | ° |
| Dynamic Range | −90-90 | ° |
| Supply Current | 0.7 | mA |

In addition to electronic bench-top verification, the automated infiltration detection system may be characterized using both lab tests and human subject experiments. Since a venipuncture is used to test whether an infusion resulting in infiltration can be sensed, various tests using venipuncture were conducted using a piece of pork belly. Pork belly has multiple layers of connective tissue and fats, and also has a roughly textured top layer similar to skin.

Figure 9:
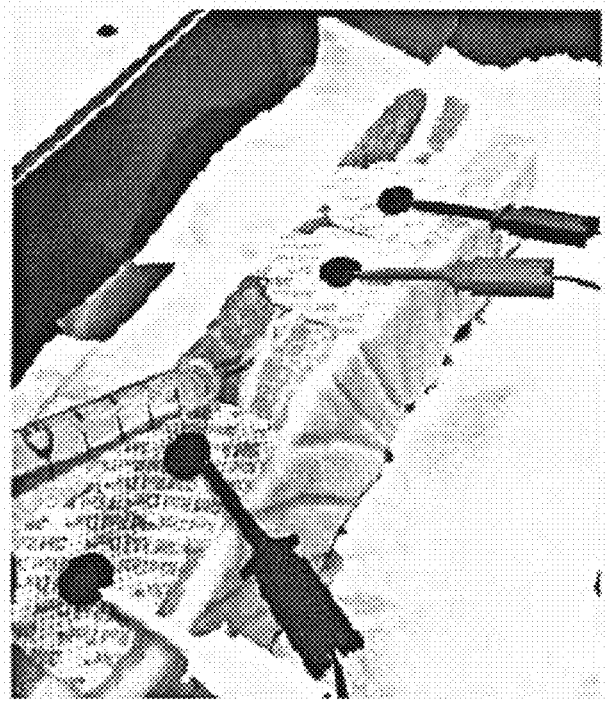
FIG. 9 shows electrodes in a tetrapolar configuration on a pork belly tissue model.
Figure 10:
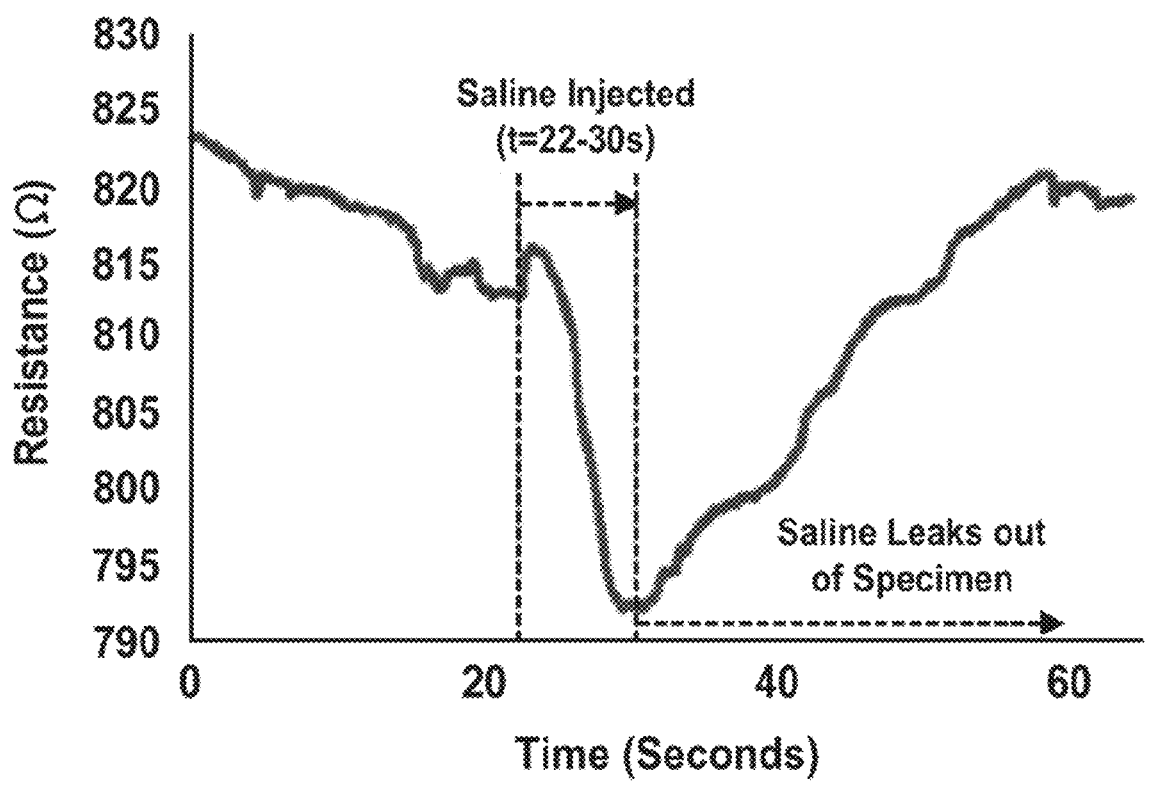
FIG. 10 shows the bioimpedance measurements taken during an infusion test in which human tissue was simulated by pork belly.

Bioimpedance may be measured by using 3M Red Dot Ag/AgCl electrodes in a tetrapolar configuration, which is illustrated in FIG. 9. A conductive liquid (3 mL volume) injected into tissue results in a decrease in bioimpedance, since the liquid content allows a lower resistance path for current to travel through the medium. FIG. 10 shows the bioimpedance measurements taken during an infusion test in which human tissue was simulated by pork belly. The bioimpedance results were positive in reacting to a liquid infusion by reducing the impedance seen. The physiological range noticed through this experiment may be −20Ω change after infusing 3 mL of conductive solution, from a pre-infusion resistance of 815Ω. This change is measurable with this system and can detect whether liquid content around the electrodes has changed by a few milliliters. The return to pre-infusion resistance level in approximately 30 seconds may be unexpected, but shows that liquid content reduces as it leaks out of the meat. Since there is no skin surrounding the meat, the pork belly model does not retain the liquid in the local area.

Figure 11:
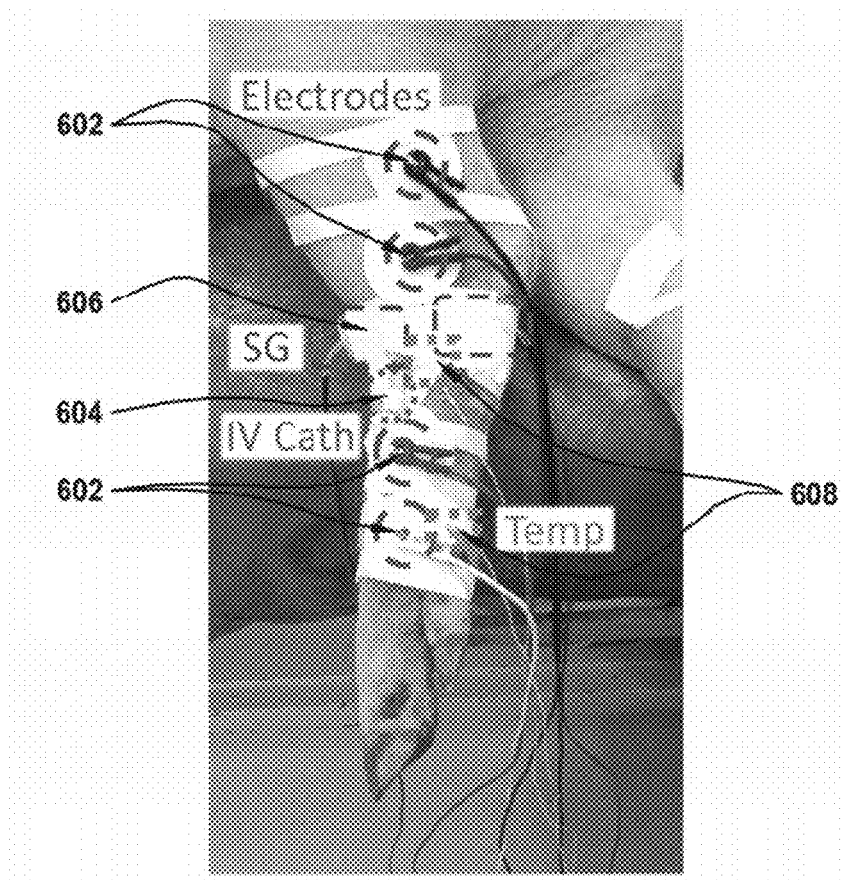
FIG. 11 shows an exemplary setup of testing multiple modalities of wearable sensors on a live pig model.
Figure 12:
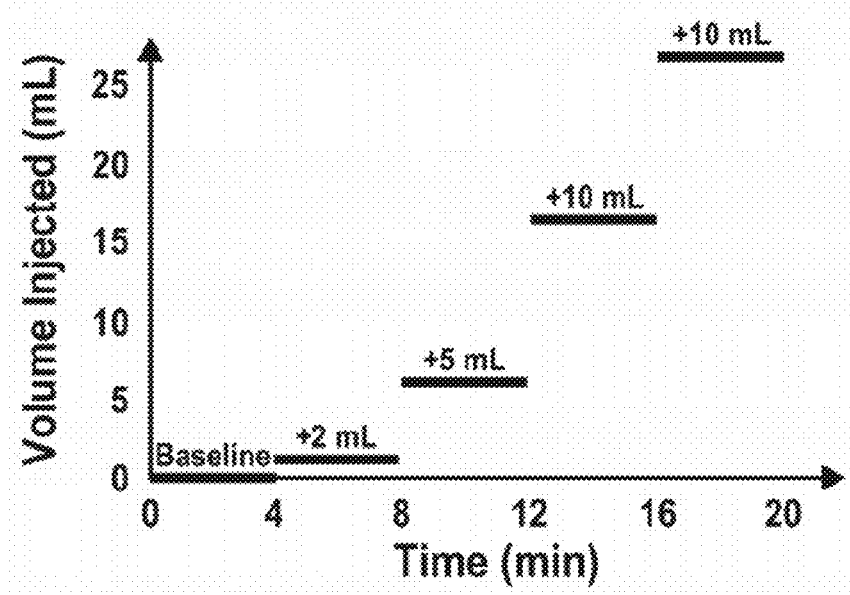
FIG. 12 is a graph of the protocol used in testing the multiple modalities of wearable sensors on the live pig model shown in FIG. 11.
Figure 13:
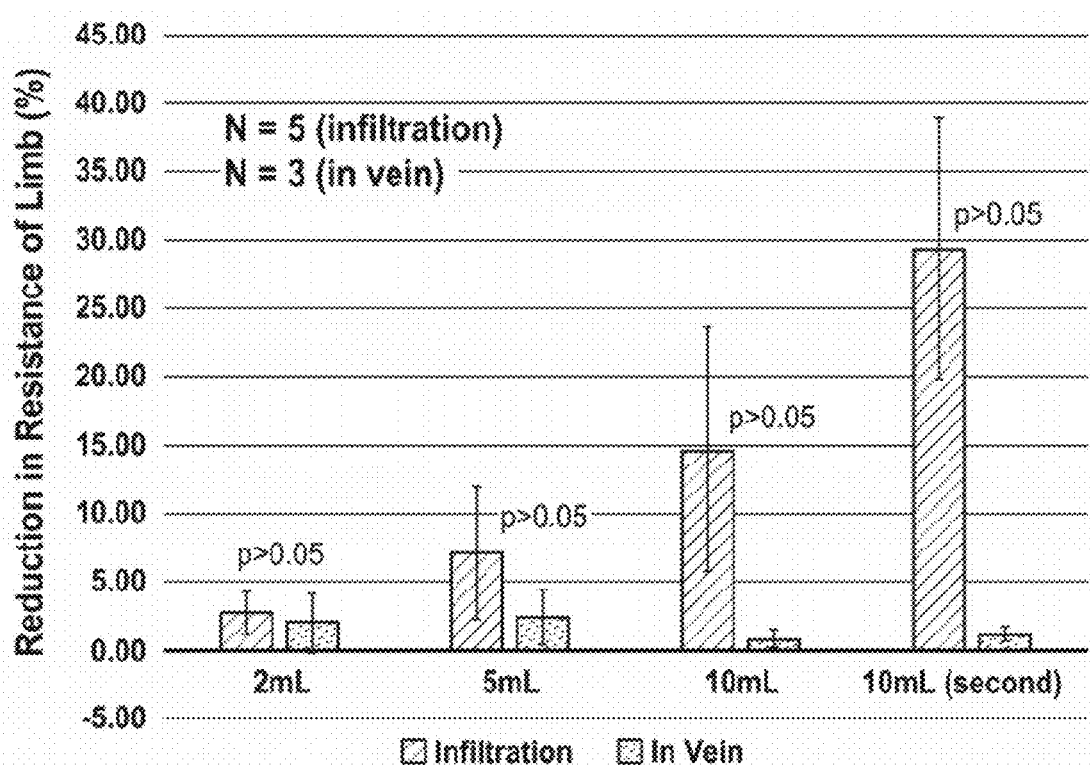
FIG. 13 is a graph showing the EBI data generated during the test of FIGS. 11-12.
Figure 14:
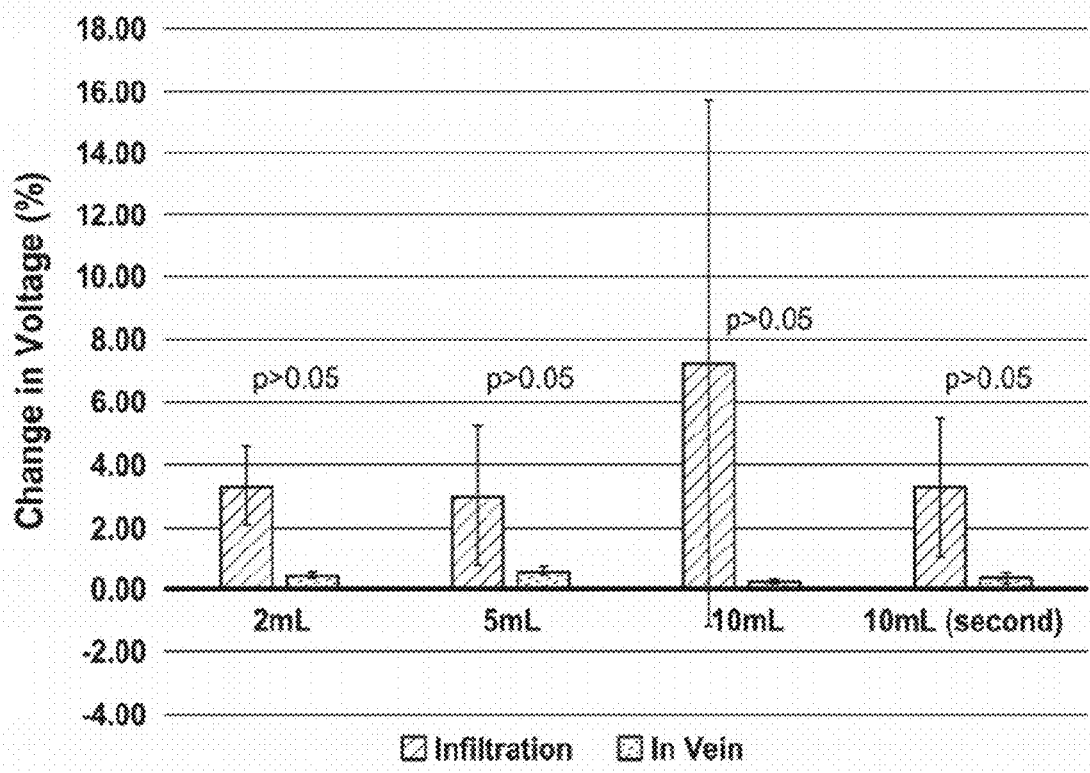
FIG. 14 is a graph showing the strain data generated during the test of FIGS. 11-12.

FIG. 11 shows an exemplary setup of the wearable sensors on a hind leg of a live, anesthetized pig. In this example, an intravenous (IV) catheter was placed either (a) in the vein or (b) in the surrounding tissue of the limb of an anesthetized pig. Successively increasing volumes of saline (2, 5, 10, and a second 10 mL boluses) were then administered into either the vein or surrounding tissue. The graph of FIG. 12 illustrates this protocol. Three modalities of sensors were placed at the limb: four Ag/AgCl gel adhesive electrodes 602 for electrical bioimpedance (EBI) measurement (two proximal to the catheter insertion site 604, and two distal to the catheter insertion site 604), two strain gauges 606, and two temperature sensors 608. FIG. 13 shows EBI measurements, normalized to the baseline resistance of the limb. The EBI measurements are presented as changes in resistance relative to these initial baseline values. A statistically significant ($p<0.05$) reduction in resistance was observed for volumes exceeding 5 mL for infiltration (saline injected into the surrounding tissue) versus injection into the vein. FIG. 14 shows strain gauge measurements, which can indicate stretching due to the fluid being infused into the surrounding tissue (infiltration). The strain gauge measurements are presented as change in voltage. Significantly significant voltage differences were observed between injection into the vein versus the tissue for all volumes injected, demonstrating that strain can be used to detect even small volumes of infiltration.

Strain may be measured by using strain gauges in a Wheatstone bridge configuration. The placement of these gauges allows for measurement in the same axial direction across all the sensors. Hence, each gauge may be placed and fixated carefully. In experimental tests, the strain results were also positive in reacting to liquid infusion. The +2.25% change (shown in FIG. 3) indicates an expansion of the pork belly after 3 mL infusion of saline. The post-infusion pull-back is also seen in the measurement, in line with the same response elicited in the bioimpedance test (due to leakage of the saline out of the pork belly model). A post-infusion pull-back, if noted in the clinic, can potentially give medical staff insightful information on how much liquid has leaked and the exact timing associated.

In an exemplary embodiment, hardware may include sensors, e.g., a strain gauge, temperature sensors, a light emitting diode (LED)/photodiode pair and a plurality of electrodes. The electrodes may be interfaced with analog "Front end" circuitry to a microcontroller for wireless transfer, e.g., via Bluetooth or other wireless technology to a computer or storage device. The system may be applied to the top of the subject's hand, for example, if an IV is inserted in to the hand, as is common.

The strain gauge may be placed on a soft plastic member at the wrist of the subject, such that swelling of the back of the hand will cause an increase in strain on a plastic cantilever, thus changing the electrical signal measured by the strain gauge and recorded, e.g., by a microcontroller. The microcontroller, may be, for example, an analog front-end circuitry using an integrated circuit, for example, an AFE4300 by Texas Instruments. Other devices for quantifying skin stretch, such as an optical measurement of the reflectivity of the skin and force sensitive resistors or flex sensors may be adhered to the skin. Other modes of skin stretch sensing may also be used, but are not required.

Temperature sensors may also be placed to enable a differential measurement. In the exemplary embodiment, for example, a temperature sensor may be placed at the wrist, next to the strain gauge, and another temperature sensor may be placed further back on the forearm, closer to the elbow. RTD sensors, such as four wire RTD sensors by Omega, may be interfaced to custom electronics for high resolution skin temperature measurement, for example, on the order of 0.1° C., although such custom electronics are not required for operation of the present system. The higher resolution offered by the custom electronics may improve detection speed and improve sensitivity and specification in detecting the effects associated with IV infiltration rather than temperature fluctuations due to changing ambient temperature, sympathetic arousal, or other confounding factors. However, customized electronics are not necessary for the present system to function. The resolution achieved by RTD sensors is sufficient, as would be any device that is below the threshold of human touch, which is the current standard of care.

According to the principles presented herein, a system or method for capturing physiological state of a user at or around a peripheral catheter insertion site may include multiple modalities of wearable sensors, a processor, and an indicator. The data collected from these wearable sensors is processed for detecting the presence of extravascular fluid, and providing an indication to a medical professional. The processor is in electrical communication with the multiple modalities of wearable sensors, and is configured to run an algorithm to process the sensor data collected from the multiple modalities of wearable sensors and to detect the presence of extravascular fluid. The indicator is in electrical communication with the processor and is configured to provide an indication of the presence of extravascular fluid.

One modality of wearable sensors includes an electrical bioimpedance (EBI) system, which includes electrodes for measuring EBI at one or multiple frequencies when positioned on the skin. Another modality of wearable sensors includes temperature sensors configured to measure skin temperature. Another modality of wearable sensors includes strain gauges configured to measure skin stretch. Another modality of wearable sensors includes accelerometers configured to measure limb position, movement, or both. Another modality of wearable sensors includes gyroscopes configured to measure limb movement. Another modality of wearable sensors includes magnetometers for detecting motion. Another modality of wearable sensors includes optical sensors configured to measure reflectance photoplethysmogram (PPG) signals. Another modality of wearable sensors includes optical sensors configured to measure near infrared spectroscopy (NIRS) of the skin. The various modalities of wearable sensors can be used alone or in combination to detect IV infiltration.

An algorithm for processing the sensor data may use limb position and movement as a context for analyzing the EBI measurements from the EBI system. The algorithm for processing the sensor data may use skin temperature as a context for analyzing the EBI measurements. The algorithm for detecting a fault from the sensor data may fuse multiple sensing modalities. Limb movement data may be used to determine appropriate intervals to collect data or place the electronics into a low power consumption "sleep mode," for power efficiency. EBI measurements may be acquired from multiple different sites around the catheter insertion site using multiple electrodes. The algorithm for detecting faults may fuse EBI measurements from multiple locations. The EBI system may be automatically calibrated at regular intervals using measurements acquired from one or more known electronic calibration impedances within the system. One or more of the calibration impedances may be in a configuration with both resistors and capacitors in parallel, similar to skin impedance. This configuration allows for calibration at multiple frequencies at once. The algorithm for processing the EBI data may detect instances where one or more of the electrodes have lost contact with the skin. The system may encompass at least two subsystems, the first subsystem capturing physiological data around the catheter site and a second subsystem capturing data at a different location (to be used as a control or reference site). The processing algorithm may compare the data acquired from the catheter insertion site to the data acquired from the reference site. Current injected through the EBI system electrodes may be monitored and if the current amplitude exceeds predefined limits, the current can be shut down. The injected current amplitude of the EBI system may be automatically adjusted per user in order to maximize resolution and use of dynamic range.

It is contemplated that a device according to the present disclosure may be designed to be in a mechanical structure to include all components and be placed near an IV catheter site regardless of position on the body. The system may take advantage of wireless communication to send information to a computer with a warning system off-body or an alarm system may be part of the on-body mechanical structure to alert medical staff of IV infiltration.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Throughout this application, various publications may have been referenced. The disclosures of these publications in their entireties are hereby incorporated by reference into this application in order to more fully describe the state of the art to which this invention pertains.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A sensor system for automated detection of intravenous (IV) infiltration, the sensor system comprising:
   a processing device comprising at least one processor and memory, wherein the processing device is configured to be physically separated from a subject such that the subject is untethered from the processing device;
   a first sensor having wireless communication capability to communicate with the processing device, the first sensor comprising one of a physiological state sensor or a movement sensor; and
   an electrical bioimpedance (EBI) sensor having wireless communication capability to communicate with the processing device,
   wherein the memory of the processing device has instructions stored thereon that, when executed by the processor, cause the processing device to:
      obtain readings from the EBI sensor and the first sensor;
      determine whether the readings from the EBI sensor are questionable using the readings from the first sensor obtained in a time frame relative to the readings from the EBI sensor; and
      detect IV infiltration based on the readings from the EBI sensor if the readings from the EBI sensor are determined not to be questionable, wherein IV infiltration is detected if the readings of the EBI sensor are within a first predetermined range.

2. The sensor system of claim 1, wherein the first sensor and the EBI sensor are configured to be positioned on the body of the subject.

3. The sensor system of claim 1, wherein the first sensor and the EBI sensor are configured to be positioned proximal to one another on the body of the subject.

4. The sensor system of claim 1, wherein the first sensor and the EBI sensor are configured to be co-located at or positioned around a peripheral catheter insertion site on the body of the subject.

5. The sensor system of claim 1, wherein the wireless communication capability is a capability to transmit readings of the respective one of the first sensor and the EBI sensor to the processing device.

6. The sensor system of claim 1, further comprising a third sensor, wherein the third sensor is a physiological state sensor.

7. The sensor system of claim 6, wherein the third sensor measures at least one of swelling, skin firmness, skin strain, and reflectance.

8. The system of claim 6, wherein the third sensor is a non-invasive, wireless sensor.

9. The sensor system of claim 8, wherein the wireless communication capability is a capability to transmit readings of the third sensor.

10. The sensor system of claim 6, wherein the determination of whether the readings of the EBI sensor are questionable is further based on readings of the third sensor obtained in the time frame relative to the readings from the EBI sensor.

11. The system of claim 6, further comprising a fourth sensor, wherein the fourth sensor is a physiological state sensor, wherein the determination of whether the readings of the EBI sensor are questionable is further based on readings of the third and fourth sensors obtained in the time frame relative to the readings from the EBI sensor.

12. The system of claim 6, wherein the first sensor, the EBI sensor, and the third sensor are configured to be co-located at or around the peripheral catheter insertion site.

13. The system of claim 6, further comprising a warning system configured to be positioned remotely from the patient.

14. The system of claim 1, further comprising a warning system configured to be positioned remotely from the patient.

15. The system of claim 14, further comprising a third sensor, wherein the third sensor is a physiological state sensor, wherein the third sensor is housed in the wearable sleeve or wrap.

16. The system of claim 1, further comprising a battery co-located with the wearable sensors for powering the wearable sensors.

17. The system of claim 1, further comprising a wearable sleeve or wrap housing at least one of the first sensor or the EBI sensor.

18. The system of claim 1, further comprising a battery co-located with the first sensor and the EBI sensor for powering the sensors.

19. The system of claim 1, wherein the physiological state sensor is a temperature sensor.

20. The system of claim 1, further comprising a warning system configured to be positioned on the body of the patient.

21. The system of claim 1, wherein the instructions further cause the system to provide an alert if the readings from the EBI sensor are determined to be questionable.

* * * * *